United States Patent [19]

Chan et al.

[11] 4,269,856
[45] May 26, 1981

[54] MITE AND MITE OVICIDAL COMPOSITIONS

[75] Inventors: David C. K. Chan, San Francisco; Arthur A. Whipp, Walnut Creek, both of Calif.

[73] Assignee: Chevron Research Company, San Francisco, Calif.

[21] Appl. No.: 74,358

[22] Filed: Sep. 10, 1979

Related U.S. Application Data

[60] Continuation of Ser. No. 912,166, Jun. 2, 1978, Pat. No. 4,208,348, which is a division of Ser. No. 760,042, Jan. 17, 1977, Pat. No. 4,107,332.

[51] Int. Cl.³ ............................................. A01N 9/16
[52] U.S. Cl. .................................................. 424/321
[58] Field of Search ................... 424/321; 260/556 A

[56] References Cited

U.S. PATENT DOCUMENTS

| | | | |
|---|---|---|---|
| 2,779,788 | 1/1957 | Gysin et al. | 424/321 |
| 2,779,941 | 1/1957 | Gysin et al. | 424/321 |
| 3,178,447 | 4/1965 | Kohn | 260/309.5 |
| 3,678,017 | 7/1972 | Shelton et al. | 260/556 A |
| 3,703,500 | 11/1972 | Nast | 260/79.5 B |
| 3,925,555 | 12/1975 | Okuda et al. | 424/321 |
| 4,068,000 | 1/1978 | Edwards | 424/321 |
| 4,092,429 | 5/1978 | Epstein et al. | 424/321 |

*Primary Examiner*—Douglas W. Robinson
*Attorney, Agent, or Firm*—D. A. Newell; T. G. DeJonghe; R. J. Suyat

[57] ABSTRACT

Mites and mite eggs are killed with an N-tetrachloroethylthio-substituted sulfonamide of the formula

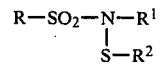

wherein R is alkyl, alkenyl, cycloalkyl or aryl, $R^1$ is alkyl, alkenyl, cycloalkyl or aryl, and $R^2$ is tetrachloroethyl, with the proviso that R and $R^1$ are not both cycloalkyl or aryl.

6 Claims, No Drawings

MITE AND MITE OVICIDAL COMPOSITIONS

This is a continuation of application Ser. No. 912,166, filed June 2, 1978, now U.S. Pat. No. 4,208,348, which in turn is a division of Ser. No. 760,042, filed Jan. 17, 1977, now U.S. Pat. No. 4,107,332.

BACKGROUND OF THE INVENTION

U.S. Pat. No. 3,178,447, issued to G. K. Kohn on Apr. 13, 1965, discloses the fungicidal activity of N-polyhaloethylthio-substituted aryl- and alkanesulfonamides.

U.S. Pat. No. 2,779,788, issued to H. Gysin et al on Jan. 29, 1957, discloses fungicidal N-trichloromethylthio-substituted chloromethanesulfonamides.

U.S. Pat. No. 3,925,555, issued to I. Okuda et al on Dec. 9, 1975, discloses the control of mites with chloromethanesulfonamides.

DESCRIPTION OF THE INVENTION

The mite and mite-ovicidal compounds of the invention are represented by the formula

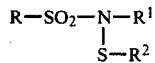

wherein R and $R^1$ individually are cycloalkyl of 5 to 8 carbon atoms substituted with up to 2 alkyl of 1 to 4 carbon atoms, alkyl of 1 to 6 carbon atoms, alkenyl of 3 to 6 carbon atoms, and phenyl or benzyl substituted with up to 2 of the same or different substituents selected from fluoro, chloro, bromo, trifluoromethyl, trichloromethyl, tribromomethyl or alkyl of 1 to 4 carbon atoms; and $R^2$ is tetrachloroethyl, with the proviso that R and $R^1$ are not both cycloalkyl or aryl.

Representative alkyl groups which R and $R^1$ may represent include methyl, ethyl, propyl, isopropyl, butyl, hexyl, etc. Representative cycloalkyl and alkylcycloalkyl which R and $R^1$ may represent include cyclopentyl, 3-methylcyclopentyl, cyclohexyl, 2,4-dimethylcyclohexyl, 4-ethylcyclohexyl, cycloheptyl, cyclooctyl, 5-methylcyclooctyl, etc. Representative alkenyl groups which R and $R^1$ may represent include allyl, 2-butenyl, 4-hexenyl, etc. Representative aryl groups which R and $R^1$ may represent include phenyl; substituted phenyl such as 4-fluorophenyl, 2-chlorophenyl, 2,4-dibromophenyl, 3-trichloromethylphenyl, 4-tribromomethylphenyl, 2,4-dimethylphenyl, 2-methyl-4-chlorophenyl, 2-methyl-4-trifluoromethylphenyl; benzyl; and substituted benzyl such as 4-chlorobenzyl, 2,4-dibromobenzyl, 4-methylbenzyl, and 3-trifluoromethylbenzyl.

Tetrachloroethyl $R^2$ groups are 1,1,2,2,-tetrachloroethyl and 1,2,2,2-tetrachloroethyl.

Preferred alkyl R or $R^1$ groups are alkyl of 1 to 4 carbon atoms. Preferred cycloalkyl R or $R^1$ groups are cycloalkyl of 5 to 6 carbon atoms substituted with up to 2 alkyl of 1 to 4 carbon atoms. Preferred aryl R or $R^1$ groups are phenyl and phenyl-substituted with 1 to 2 of the same or different substituents selected from fluoro, chloro, bromo, trifluoromethyl or alkyl of 1 to 2 carbon atoms. The most preferred aryl R or $R^1$ groups are phenyl and phenyl-substituted with 1 to 2 fluoro, chloro or bromo. The preferred $R^2$ group is 1,1,2,2-tetrachloroethyl.

One class of preferred compounds of formula (I) is that wherein one R or $R^1$ group is cycloalkyl, especially cycloalkyl of 5 to 6 carbon atoms and the other R or $R^1$ group is alkyl, especially alkyl of 1 to 4 carbon atoms.

Another preferred class of compounds is that wherein one R or $R^1$ group is aryl (phenyl or substituted phenyl), especially phenyl substituted with up to 2 of the same or different substituents selected from fluoro, chloro, bromo, trifluoromethyl or alkyl of 1 to 2 carbon atoms, and the other R or $R^1$ group is cycloalkyl, especially cycloalkyl of 5 to 6 carbon atoms.

Another preferred class of compounds is that wherein one R or $R^1$ group is phenyl or phenyl substituted with up to 2 of the same or different substituents selected from fluoro, chloro, bromo, trifluoromethyl, trichloromethyl, tribromomethyl or alkyl of 1 to 2 carbon atoms, and the other R or $R^1$ group is alkyl, especially alkyl of 1 to 4 carbon atoms.

Another preferred class of compounds is that wherein one R or $R^1$ group is alkenyl.

The most preferred class of compounds is that wherein R is alkyl of 1 to 6 carbon atoms, preferably of 1 to 4 carbon atoms, $R^1$ is phenyl and $R^2$ is tetrachloroethyl, preferably 1,1,2,2-tetrachloroethyl.

Representative compounds of the invention include
N-cyclohexyl-N-(1,1,2,2-tetrachloroethylthio)-allylsulfonamide
N-cyclopentyl-N-(1,1,2,2-tetrachloroethylthio)-4-chlorophenylsulfonamide
N-4-methylcycloheptyl-N-(1,1,2,2-tetrachloroethylthio)-isopropanesulfonamide
N-methyl-N-(1,1,2,2-tetrachloroethylthio)-ethanesulfonamide
N-ethyl-N-(1,1,2,2-tetrachloroethylthio)-cyclopentanesulfonamide
N-sec-butyl-N-(1,1,2,2-tetrachloroethylthio)-4-tribromomethylphenylsulfonamide
N-allyl-N-(1,1,2,2-tetrachloroethylthio)-allylsulfonamide
N-allyl 2-butenyl-N-(1,1,2,2-tetrachloroethylthio)-cyclohexanesulfonamide
N-phenyl-N-(1,1,2,2-tetrachloroethylthio)-2-hexenesulfonamide
N-2,4-dichlorophenyl-N-(1,1,2,2-tetrachloroethylthio)-cyclohexanesulfonamide
N-cyclohexyl-N-(1,2,2,2-tetrachloroethylthio)-methanesulfonamide, and
N-ethyl-N-(1,2,2,2-tetrachloroethylthio)-cyclohexanesulfonamide.

The compounds of the invention are prepared by sulfenylating a sulfonamide of the formula $R-SO_2-NH-R^1$ (II), wherein R and $R^1$ have same significance as previously defined, with a tetrachloroethylsulfenyl halide, e.g., 1,1,2,2-tetrachloroethylsulfenyl chloride or 1,2,2,2-tetrachloroethylsulfenyl chloride. The sulfenylation reaction is conducted by reacting substantially equimolar quantities of the sulfonamide (II) and the sulfenyl halide in the liquid phase in the presence of an acid acceptor. Suitable acid acceptors are organic amines such as pyridine compounds, e.g., pyridine or alpha-picoline, and lower trialkylamines, e.g., triethylamine or tributylamine, and inorganic alkali metal hydroxides, e.g., sodium hydroxide or potassium hydroxide. Generally, at least one mol of acid acceptor is employed for each mol of tetrachloroethylsulfenyl halide. The reaction is normally conducted in an inert liquid diluent, e.g., organic solvents such as chlorinated hydrocarbons.

Preferably, the reaction is conducted in the presence of catalytic amounts of a quaternary ammonium salt.

Generally, amounts of quaternary ammonium salt per mol of the sulfenyl halide reactant vary from about 0.01 to 0.3, although amounts from 0.05 to 0.2 mol per mol of the sulfenyl halide are preferred. Suitable quaternary ammonium salts are tetraalkylammonium halides wherein the alkyl has 1 to 6 carbon atoms and the halide is fluoro, chloro, bromo or iodo, e.g., tetramethaneammonium chloride or tetrabutylammonium bromide.

In order to prepare the compounds of the invention wherein one R or $R^1$ group is cycloalkyl and the other R or $R^1$ is alkyl, it is essential that catalytic amounts of the quaternary ammonium salt be employed.

The sulfenylation reaction is conducted at a temperature of 0° C. to the boiling point of the diluent, although temperatures between 0° C. and 100° C. are preferred. The reaction is conducted at or above atmospheric pressure. The reaction time will, of course, vary depending on the reaction temperature and the particular reactants employed. Generally, the reaction is completed within one-half to 24 hours. The product (I) is isolated and purified by conventional procedures such as extraction, filtration, crystallization and chromatography.

The compounds of the invention have been found to be useful and effective for the killing of mite eggs. Some compounds of the invention are also useful and effective for the killing of mites. The compounds of the invention also have excellent activity against fungi.

Any conventional techniques or methods can be employed for contacting mites or mite eggs with an effective miticidal or ovicidal amount of the compounds of the invention. Like most agricultural chemicals, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts, or granules to the mites or mite eggs, their environment or hosts susceptible to mite attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5-80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other higher absorbent, readily wet, inorganic diluents. Typical wetting, dispersing, or emulsifying agents used in agricultural formulations include, for example, the alkyl and alkylaryl sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains 75% silica and 25% of the toxicant.

Useful liquid concentrates include the emulsifiable concentrates, which are homogenous liquid or paste compositions which are readily dispersed in water to other dispersant, and may consist entirely of the toxicant with a liquid or solid emulsifying agent, or may also contain a liquid carrier, such as xylene, heavy aromatic naphthas, isophorone, and other non-volatile organic solvents. For application these concentrates are dispersed in water or other liquid carrier, and normally applied as a spray to the area to be treated.

The percentages by weight of the toxicant may vary according to the manner in which the composition is to be applied and the particular type of formulation, but in general comprises 0.5% to 95% of the toxicant by weight of the pesticidal composition.

The compositions may be formulated and applied with other active ingredients, including nematocides, insecticides, fungicides, bactericides, plant growth regulators, fertilizers, etc. In applying the chemical an effective amount and concentration of the toxicants of this invention is, of course, employed.

EXAMPLES

EXAMPLE 1

Preparation of N-hexyl-N-(1,1,2,2-tetrachloroethylthio)-propanesulfonamide

A 3.8 g (0.047 mol) sample of 50% weight aqueous sodium hydroxide solution was added dropwise to a cooled (8° C.) solution of 9.0 g (0.043 mol) N-hexyl propanesulfonamide and 11.0 g (0.047 mol) 1,1,2,2-tetrachloroethylsulfenyl chloride in 150 ml dichloromethane. After the addition was completed, the reaction was stirred at about 25° C. for 4 hours during which time a precipitate formed. The reaction mixture was then washed with water, dried over magnesium sulfate and evaporated under reduced pressure to give an oily residue. The residue was chromatographed through 250 g silica gel with 10% ethylether/90% hexane elution to give 7 g of the product as a yellow oil. The elemental analysis for the product showed: %S, calc. 15.8, found 16.2; %Cl, calc. 35.0, found 33.5. The product is tabulated in Table I as Compound No. 1.

EXAMPLE 2

Preparation of N-cyclohexyl-N-(1,1,2,2-tetrachloroethylthio)-isopropanesulfonamide A 2.4 g (0.29 mol) sample of 50% weight aqueous sodium hydroxide solution was added dropwise to a cooled (12° C.) solution of 5.6 g (0.027 mol) N-cyclohexyl-isopropanesulfonamide, 7 g (0.029 mol) 1,1,2,2-tetrachloroethylsulfenyl chloride and 0.5 g benzyl triethylammonium chloride in 150 ml methylene chloride. A precipitate formed in the reaction mixture during the first 10 minutes of the addition. After the addition was completed, the reaction mixture was allowed to warm to room temperature and stirred for one hour. The reaction mixture was then washed with water, dried over magnesium sulfate and evaporated under reduced pressure to give the reaction product. The reaction product was chromatographed through 250 g silica gel with 50% chloroform/50% hexane elution to give 4 g (37%) of N-cyclohexyl-N-(1,1,2,2-tetrachloroethylthio)-isopropanesulfonamide, m.p. 122°–123° C. This reaction is tabulated in Table II as Run No. 1.

The above reaction was repeated under identical conditions except that the benzyl triethylammonium chloride catalyst was omitted and the reaction mixture was stirred at 25° C. for 3 hours instead of one hour. Workup and analysis of the reaction mixture by nuclear magnetic resonance spectroscopy (comparison with the authentic material) showed that no sulfenylated sulfonamide product was obtained. This reaction is tabulated in Table II as is Run No. 1A.

The remaining reactions tabulated in Table II were conducted by procedures essentially identical to the reactions described in Example 2.

EXAMPLE 3

Two-Spotted Mite Control Tests

Compounds of the invention were tested for the control mites and mite eggs by the following procedure.

Pinto bean leaves were infested with two-spotted mites (*Tetramuchus urticae*). The mites were then allowed to lay eggs on the leaves. After 48 hours, the leaves were dipped into a water/acetone solution containing a small amount of a nonionic surfactant and 40 ppm of the test compound. The treated leaves were then maintained at 85° F. One day after treatment, the mortality of adult mites was determined, and seven days after treatment, the egg mortality (non-hatching eggs) was determined.

The results for the compounds found to have mite and mite-egg control activity are tabulated in last column of Tables I and II.

EXAMPLE 4

Texas Citrus Mite Control

Representative compounds of the invention were tested for the control of Texas citrus mites (*Eutetranychus banksi*) on 18-year-old Hamlin citrus trees by the following procedure: single branches containing no new growth were sprayed with an aqueous solution containing from 0.5 lb to 2 lbs of a 50% wt. wettable formulation of the test compound (50% weight test compound in talc and a small amount of a wetting agent) in 100 gallons water. The branches were sprayed until both leaf surfaces were dripping wet. Five branches were sprayed at each test concentration. The total number of live mites on the sprayed branches and untreated test branches (sprayed with water only) was determined at periodic intervals by examining one square inch per leaf (top surface) on ten leaves (2 leaves from each sprayed branch). The results are tabulated in Table III.

EXAMPLE 5

European Red Mite Control

Representative compounds of the invention were tested for the control of European red mites (*Panonqychus ulmi*) on 11-year-old red delicious (Starkrimson) apple trees by the following procedure: The trees were sprayed to run-off (3 gal. per tree) with an aqueous solution containing 1 lb of test compound per 100 gals. water. At periodic intervals 25 leaves were picked from each tree and counts made of mites and mite eggs. The test compound, the adult, nymph and egg counts, and the days after treatment are tabulated in Table IV.

EXAMPLE 6

Texas Citrus Mite & Citrus Rust Mite Control

N-propyl-N-(1,1,2,2-tetrachloroethylthio)-phenylsulfonamide (Compound No. 5, Table I) was tested for the control of Texas citrus mites (*Eutetranychus banksi*) and citrus rust mites (*Phyllocaptrata oleivora*) on citrus trees (Parson Brown) by the following procedure: The citrus trees (21 years old, 18 feet tall) were sprayed (9 gal/tree) 4 weeks after petal fall with an aqueous solution containing 0.25 to 1 lb of the test compound per 100 gallons water. The test compound was formulated as a 50% wt. wettable powder in talc and a small amount of a wetting agent. Four trees were employed for each test concentration. At periodic intervals after spraying, 10 leaves were randomly picked from each tree and the number of live mites was determined. The percent control was calculated from the mite count of treated trees divided by the mite count of untreated trees. The results are tabulated in Table V.

TABLE I

Compounds of the Formula R—SO$_2$—N—R$^1$
                              |
                              S—R$^2$

| Compound No. | R | R$^1$ | R$^2$ | Melting Point, °C. | Mite Control Adult | Mite Control Eggs |
|---|---|---|---|---|---|---|
| 1 | n-C$_3$H$_7$ | n-C$_6$H$_{13}$ | CCl$_2$CCl$_2$H | oil | 39 | 100# |
| 2 | C$_2$H$_5$ | p-Cl—φ* | " | 126–128 | 0 | 100 |
| 3 | φ | CH$_3$ | " | 81–83 | 94 | 100 |
| 4 | C$_2$H$_5$ | φ | " | 120–121 | 0 | 100 |
| 5 | n-C$_3$H$_7$ | φ | " | 98–99 | 0 | 100 |
| 6 | i-C$_3$H$_7$ | φ | " | 99–100 | 96 | 100 |
| 7 | n-C$_4$H$_9$ | φ | " | 70–71 | 0 | 50 |
| 8 | φ | s-C$_4$H$_9$ | " | oil | 96 | 100 |
| 9 | C$_2$H$_5$ | pCF$_3$—φ | " | 118–119 | 0 | 85 |
| 10 | p-CH$_3$—φ | CH$_3$ | " | 112–114 | 0 | 30 |
| 11 | i-C$_4$H$_9$ | φ | " | 110–112 | 0 | 85 |
| 12 | C$_2$H$_5$ | m-CF$_3$—φ | " | 100–101 | 90 | 100 |
| 13 | C$_2$H$_5$ | m-CH$_3$—φ | " | 60–62 | 85 | 100 |
| 14 | C$_2$H$_5$ | m-(i-C$_3$H$_7$)—φ | " | 110–111 | 0 | 60 |
| 15 | n-C$_{10}$H$_{21}$ | φ | " | oil | 0 | 0 |

TABLE I-continued

Compounds of the Formula R—SO$_2$—N(R$^1$)—S—R$^2$

| Compound No. | R | R$^1$ | R$^2$ | Melting Point, °C. | Mite Control Adult | Mite Control Eggs |
|---|---|---|---|---|---|---|
| 16 | n-C$_3$H$_7$ | m-(i-C$_3$H$_7$)—φ | " | 139–141 | 11 | 0 |
| 17 | C$_2$H$_5$ | 3,5-(CF$_3$)—φ | " | 101–102 | 78 | 50 |
| 18 | 2,4-Cl$_2$—φCH$_2$ | CH$_3$ | " | 82–89 | 0 | 85 |
| 19 | CH$_3$ | φ | " | 124–126 | 0 | 100 |
| 20 | s-C$_4$H$_9$ | φ | " | 76–77 | 90 | 99 |
| 21 | C$_2$H$_5$ | φ | CHClCCl$_3$ | 78–85 | 0 | 15 |
| 22 | n-C$_3$H$_7$ | φ | " | 84–88 | 100 | 100 |
| 23 | cyclohexyl | φ | CCl$_2$CCl$_2$H | 112–115 | 0 | 85 |
| 24 | cyclohexyl | m-CH$_3$—φ | " | 94–95 | 0 | 60 |
| 25 | CH$_2$=CH | φ | " | 106–111 | 0 | 94 |
| 26 | CH$_3$—C(CH$_3$)=CH— | φ | " | 116–117 | 0 | 100 |
| 27 | cyclohexyl | m-CH$_3$—φ | " | 94–95 | 0 | 60 |
| 28 | C$_2$H$_5$ | cyclohexyl | CCl$_3$ | 66–68 | 0 | 0 |
| 29 | φ | φ | CCl$_3$ | 142–143 | 0 | 0 |
| 30 | 2,5-Cl$_2$—φ | 4-CF$_3$—φ | CCl$_3$ | 101–103 | 0 | 0 |
| 31 | C$_2$H$_5$ | 3,5-(CF$_3$)$_2$—φ | CCl$_3$ | 100–101 | 0 | 0 |
| 32 | cyclohexyl | cyclohexyl | CCl$_2$CCl$_2$H | 135–137 | 0 | 0 |

*φ represents phenyl
100 ppm

TABLE II

| Run No. | RSO$_2$NHR$^1$ R | RSO$_2$NHR$^1$ R$^1$ | CHCl$_2$CCl$_2$SCl Mols | NaOH Mols | Salt* Mols | CH$_2$Cl$_2$ Ml | Reaction Conditions Hr | Reaction Conditions °C | Yield | Melting Point, °C | Mite Control Adults | Mite Control Eggs |
|---|---|---|---|---|---|---|---|---|---|---|---|---|
| 1 | i-C$_3$H$_7$ | phenyl | 0.027 | 0.029 | 0.029 | 0.002 | 150 | 1 | 12–25 | 37% | 122–123 | 78% | |
| 2 | n-C$_3$H$_7$ | phenyl | 0.04 | 0.043 | 0.058 | 0.002 | 200 | 2½ | 12–25 | 45% | 78–80 | 0 | 15% |
| 3 | cyclohexyl | i-C$_3$H$_7$ | 0.027 | 0.027 | 0.027 | 0.002 | 150 | 3 | 12–25 | 32% | 85–87 | 0 | 100% |
| 4 | n-C$_3$H$_7$ | CH$_3$-phenyl | 0.046 | 0.047 | 0.047 | " | " | 3 | " | 25% | 66–70 | 70% | 99% |
| 5 | i-C$_3$H$_7$ | CH$_3$-phenyl | 0.046 | 0.047 | 0.047 | " | " | 3 | " | 13% | 76–78 | 90% | 96% |
| 6 | s-C$_4$H$_9$ | phenyl | 0.031 | 0.031 | 0.031 | " | " | 2 | " | 19% | 58–59 | 90% | 78% |
| 7 | CH$_3$ | CH$_3$-phenyl | 0.037 | 0.038 | 0.038 | " | " | 2 | " | 63% | 105–108 | 90% | 100% |
| 8 | C$_2$H$_5$ | CH$_3$-phenyl | 0.039 | 0.043 | 0.043 | " | " | 2 | " | 25% | 79–87 | 98% | 30% |
| 9 | CH$_3$ | cyclopentyl | 0.037 | 0.038 | 0.038 | " | " | 2 | " | 50% | 80–81 | 45% | 100% |
| 10 | CH$_3$ | cyclohexyl | 0.05 | 0.05 | 0.05 | " | " | 1 | " | 37% | 119–120 | 85% | 100% |
| 1A | i-C$_3$H$_7$ | phenyl | 0.027 | 0.027 | 0.027 | 0 | 150 | 1 | 12–25 | 0% | — | — | — |
| 2A | n-C$_3$H$_7$ | phenyl | 0.04 | 0.043 | 0.043 | 0 | 200 | 2 | 12–25 | <1% | — | — | — |

TABLE II-continued

| Run No. R | RSO₂NHR¹ | | CHCl₂CCl₂SCl Mols | NaOH Mols | Salt* Mols | CH₂Cl₂ Ml | Reaction Conditions | | Yield | Melting Point, °C. | Mite Control | |
|---|---|---|---|---|---|---|---|---|---|---|---|---|
| | R¹ | Mols | | | | | Hr | °C. | | | Adults | Eggs |
| 3A  | i-C₃H₇ | 0.027 | 0.027 | 0.027 | 0 | 150 | 3 | 12-25 | 0% | — | — | — |

TABLE III

Texas Citrus Mite Control

| Compound No. | Amount Test Compounds/100 Gal. | No. Texas Citrus Mites/10 Leaves | | | | | |
|---|---|---|---|---|---|---|---|
| | | 1 day | 2 day | 4 day | 7 day | 10 day | 17 day |
| #9-Table I | 0.25 lb. | 257 | 174 | 77 | 98 | 108 | 43 |
| | 5 | 176 | 129 | 124 | 96 | 117 | 12 |
| | 1 | 143 | 66 | 56 | 121 | 85 | 9 |
| #11-Table I | 0.25 lb. | 260 | 177 | 92 | 69 | 121 | 38 |
| | 5 | 228 | 108 | 159 | 127 | 99 | 20 |
| | 1 | 205 | 77 | 76 | 85 | 76 | 36 |
| #19-Table I | 0.25 lb. | 368 | 267 | 101 | 93 | 50 | 51 |
| | 5 | 227 | 135 | 88 | 217 | 86 | 50 |
| | 1 | 147 | 65 | 56 | 120 | 57 | 37 |
| #20-Table I | 0.25 lb. | 200 | 74 | 51 | 73 | 99 | 94 |
| | 5 | 136 | 20 | 53 | 63 | 86 | 16 |
| | 1 | 114 | 51 | 29 | 69 | 69 | 17 |
| #23-Table I | 0.25 lb. | 314 | 248 | 142 | 109 | 247 | 59 |
| | 5 | 182 | 129 | 144 | 142 | 147 | 137 |
| | 1 | 168 | 63 | 52 | 69 | 110 | 43 |
| #1-Table II | 0.25 lb. | 427 | 200 | 51 | 36 | 63 | 45 |
| | 5 | 101 | 73 | 45 | 55 | 79 | 6 |
| | 1 | 161 | 37 | 44 | 105 | 95 | 10 |
| #5-Table II | 0.25 lb. | 136 | 41 | 18 | 36 | 68 | 49 |
| | 5 | 146 | 43 | 19 | 11 | 109 | 17 |
| | 1 | 75 | 9 | 10 | 2 | 23 | 11 |
| #10-Table II | 0.25 lb. | 387 | 218 | 20 | 56 | 59 | 40 |
| | 5 | 146 | 37 | 23 | 16 | 34 | 7 |
| | 1 | 75 | 9 | 10 | 2 | 23 | 11 |
| Untreated Check | 0 | 1110 | 887 | 995 | 484 | 260 | 169 |

TABLE IV

European Red Mite Control

| Compound No. | Eggs/Leaf | | | Adults and Nymphs/Leaf | | | | | |
|---|---|---|---|---|---|---|---|---|---|
| | 0 day | 8 days | 14 days | 7 days | 13 days | 25 days | 32 days | 37 days | 60 days |
| #5-Table I | 63 | 21 | 7 | 2 | 2 | 11 | 125 | — | — |
| #20-Table I | 74 | 29 | 19 | 1 | 1 | 1 | 0 | 4 | 4 |
| #5-Table II | 72 | 8 | 1 | 1 | 0 | 1 | 4 | 12 | 5 |
| #10-Table II | 113 | 37 | 5 | 2 | 1 | 1 | 1 | 7 | 4 |
| Untreated Check | 67 | 139 | 85 | 69 | 62 | 470 | 235 | 152 | 1 |

TABLE V

Texas Citrus and Citrus Rust Mite Control

| Test Conc. lb/100 Gal. | Percent Texas Citrus Mite Control | | | | | | |
|---|---|---|---|---|---|---|---|
| | 6 days | 13 days | 20 days | 27 days | 39 days | 49 days | 63 days |
| 0.25 | 99 | 100 | 97 | 95 | 87 | 89 | 0 |
| 0.5 | 99 | 98 | 100 | 96 | 98 | 92 | 81 |
| 1.0 | 100 | 96 | 98 | 93 | 100 | 100 | 96 |

| | Percent Citrus Rust Mite Control | | | | | | |
|---|---|---|---|---|---|---|---|
| | 42 days | 49 days | 63 days | 77 days | 99 days | 105 days | 126 days |
| 0.25 | 100 | 84 | 87 | 77 | 71 | 42 | 0 |
| 0.5 | 100 | 87 | 100 | 98 | 95 | 80 | 0 |
| 1.0 | 100 | 80 | 100 | 100 | 85 | 95 | 17 |

What is claimed is:

1. A mite ovicidal composition comprising a biologically inert carrier and an ovicidally effective amount of a compound of the formula:

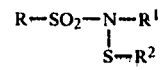

wherein one R or R¹ group is cycloalkyl of 5 to 8 carbon atoms substituted with up to 2 alkyl of 1 to 4 carbon atoms or alkenyl of 3 to 6 carbon atoms and the other R or R$^1$ group is alkyl of 1 to 6 carbon atoms, alkenyl of 3 to 6 carbon atoms, or phenyl or benzyl substituted with up to 2 of the same or different substituents selected from the group consisting of fluoro, chloro, bromo, trifluoromethyl, trichloromethyl, tribromomethyl and alkenyl of 1 to 2 carbon atoms; and R$^2$ is tetrachlorethyl.

2. The composition of claim 1 wherein one R or R$^1$ is cycloalkyl and the other R or R$^1$ is alkyl.

3. The composition of claim 1 wherein R is alkyl of 1 to 3 carbon atoms and R$^1$ is cycloalkyl of 5 to 6 carbon atoms.

4. The composition of claim 1 wherein R is alkyl of 1 to 3 carbon atoms, R$^1$ is cycloalkyl of 5 to 6 carbon atoms and R$^2$ is 1,1,2,2-tetrachloroethyl.

5. The composition of claim 1 wherein one R or R$^1$ group is phenyl substituted with up to 2 of the same or different substituents selected from the group consisting of fluoro, chloro, bromo, trifluoromethyl, trichloromethyl, tribromomethyl, and alkyl of 1 to 2 carbon atoms and the other R or R$^1$ group is cycloalkyl.

6. The composition of claim 1 wherein one R or R$^1$ group is alkenyl.

* * * * *